United States Patent [19]

Miwa

[11] Patent Number: 4,974,607
[45] Date of Patent: Dec. 4, 1990

[54] SYSTEM FOR CENTRALIZED MANAGEMENT OF MEDICAL DATA

[76] Inventor: Satoru Miwa, Maison Maruyama No. 503, 115-1, Maruyama 2-chome, Miyazaki-shi, Miyazaki, Japan

[21] Appl. No.: 184,581

[22] Filed: Apr. 21, 1988

[30] Foreign Application Priority Data

Aug. 20, 1987 [JP] Japan .................. 62-208019

[51] Int. Cl.⁵ .......................... H04M 11/00
[52] U.S. Cl. .................. 128/904; 128/670; 128/903
[58] Field of Search .............. 128/670, 903, 904

[56] References Cited

U.S. PATENT DOCUMENTS

| 3,572,316 | 3/1971 | Vogelman et al. | 128/903 |
| 3,646,606 | 2/1972 | Buxton et al. | 128/670 |
| 3,910,257 | 10/1975 | Fletcher et al. | 128/670 |
| 4,535,783 | 8/1985 | Marangoni | 128/711 |
| 4,608,994 | 9/1986 | Ozawa et al. | 128/670 |

FOREIGN PATENT DOCUMENTS

| 0212278 | 3/1987 | European Pat. Off. | 128/670 |
| 2534132 | 4/1984 | France | 128/670 |
| 2535964 | 5/1984 | France | 128/670 |

Primary Examiner—Lee S. Cohen
Assistant Examiner—Kennedy J. Schaetzle
Attorney, Agent, or Firm—Michael L. Keller; James R. Longacre

[57] ABSTRACT

A system for centralized management of medical data regarding bio-body information detected from a patient by way of a telephone line to a data processing facility in a medical organization, in which a transmission section is attached to a patient and a receiving section connected on a wireless mode to the transmission section, in which at least one of the transmission and the receiving sections has a RAM for storing general standard ranges and personal permissible ranges for bio-body information, and a CPU for comparing the bio-body information data detected from a patient with the general standard ranges and with the personal permissible ranges and outputting the detected data judged to be abnormal from the transmission section to the medical organization.

2 Claims, 5 Drawing Sheets

2

SYSTEM FOR CENTRALIZED MANAGEMENT OF MEDICAL DATA

BACKGROUND OF THE INVENTION

1. Field of the Invention

The present invention concerns a system for centralized management of medical data for bio-body information detected from individual patients, etc. More specifically, it relates to a system which is connected by way of a telephone line to a data processing facility in a hospital or like other medical organization for the centralized management of respective medical data detected from individual patients at home, and adapted to automatically send out required medical data to the telephone line.

2. Description of the Prior Art

A system for centralized management of medical data of individual in-patients is known in which various types of sensors are attached to each of a number of patients for measuring bio-body information, e.g., electrocardiogram, body temperature, blood pressure, etc. and the medical data detected from the patient are displayed on monitors placed in a central monitoring room for the monitor or diagnosis of disease.

However, such a type of medical service or nursery can be provided only for in-patients and patients who are at home. If such a patient feels an abnormality, they have to call on clinics, hospitals, etc. for ambulatory treatment or contact doctors for sick-visiting.

For overcoming the foregoing problems, there has been proposed, for example, a system in which a medical sensor such as an electrocardiography is attached to a patient who is at home (hereinafter referred to as an "at-home patient") and abnormal sensor signals, if detected, are automatically informed to a home doctor, etc. by utilizing a telephone circuit (Japanese Patent Laid-Open No. Sho 60-26126).

This prior system comprises a bio-body data measuring section including an electrocadiograph, etc, a section for recognizing the result of the measurement as to if it is normal or abnormal, a section for judging whether the abnormality is transient or persistent and a control section for driving a telephone set automatically by the signals from the detection section.

In such a system, when abnormal detection signals are detected continuously from a patient, the telephone set is driven to connect with that of a medical organization by way of a telephone line to automatically communicate the abnormal state of the patient.

However, the proposed system functions merely as an abnormality detection device and can not be utilized for sampling and using basic ordinary data of a patient which are useful to his diagnosis, etc. Referring also to the abnormality detection per se, it merely informs of various abnormal data, not selectively, and sends out miscellaneous information having no substantial abnormality together, making it difficult for effective and smooth administration of the system in practical use.

Further, since the patient is cable-connected with the telephone set by way of the measuring section, abnormality recognizing section, control section, etc., his physical movements are greatly restricted. Disconnection or like other failures may tend to occur due to lengthy connection cables, etc.

The object of the present invention is to provide a system for centralized management of medical data capable of continuously accumulating ordinary basic medical data of a patient, sending the accumulated data periodically or at a predetermined time interval by way of a telephone line to a clinic, hospital or like other medical organization, as well as rapidly informing of abnormal medical data, if detected from the patient, thereby providing an overall effect as the medical aid system for at-home patients etc.

Another object of the present invention is to provide a system for centralized management of medical data capable of surely judging, among various abnormal data, only those data that are substantially abnormal in the sense requiring urgent information to the medical facility regarding a patient pertinent to the system and selectively sending out such data by way of a telephone line to a hospital, etc.

A further object of the present invention is to provide a system for the management of personal medical data which can set a patient free from the restriction to the system as much as possible.

The foregoing object of the present invention can be attained according to this invention by a system for centralized management of medical data regarding bio-body information detected from a patient by way of a telephone line to the data processing facility in a hospital, clinic or like other medical organization, wherein the system comprises:

a transmission section having a plurality of sensors for detecting various bio-body data from a patient and a receiving section which is adapted to receive the signals of the bio-body data sent out from the transmission section and which is connected with an external telephone line through an input/output interface, in which at least one of the transmission sections and the receiving section has memory means for storing the medical data of various detected bio-body data for a predetermined period of time, and memory means for previously storing those values showing standard ranges regarding the respective bio-body information for comparison with detected values, and a judging section for comparing the respective bio-body information detected by the respective sensors with the values of the standard ranges previously stored in the memory means, and the receiving section has:

a control section adapted to read out and send the medical data accumulated in the memory means periodically or at a predetermined time interval to the telephone line, and send out the medical data the values of which are out of the standard ranges and judged to be abnormal by the judging section to the telephone line, in which the medical data are sent to the telephone line under the control of the system or upon access from the data processing facility in a medical organization, etc.

Another object of the present invention can be attained according to this invention by a system for centralized management of medical data regarding bio-body information detected from a patient by way of a telephone line to the data processing facility in a hospital, clinic or like other medical organization, wherein the system comprises:

a transmission section having a plurality of sensors for detecting the bio-body information from a patient and a receiving section which is adapted to receive the signals of the bio-body data sent out from the transmission section and which is connected with an external telephone line through an input/output interface, in which at least one of the transmission section and the receiving section has first memory means for storing the medical data of detected various bio-body data for a predetermined period of time and second memory means for previously storing those values showing general standard ranges and personal standard ranges of a patient pertinent to the system regarding respective bio-body information, as well as a first judging, section for comparing the respective bio-body data detected by the respective sensors with the values of the general standard ranges previously stored in the second memory means and a second judging section for comparing the respective bio-body information detected by the respective sensors with the values of personal standard ranges stored in the second memory means, and the receiving section has:

a control section adapted to read out and send the medical data accumulated in the first memory means periodically or at a predetermined time interval to the telephone line, and send out the medical data the values of which are out of the standard ranges and judged to be abnormal by the judging section to the telephone line, in which the medical data are sent to the telephone line under the control of the system or upon access from the side of the data processing facility in the medical organization, etc.

In the system according to the present invention, various bio-body informations of a particular patient are detected by a plurality of sensors attached to the patient such as electrocardiograph, sphygmomanometer, thermometer, etc. The detected bio-body data are continuously stored in the first memory means for a predetermined period of time and read out, when necessary, and sent to a medical organization by way of a telephone line on one hand. The detected bio-body data is compared with standard values previously stored in the second memory means, for example, general standard values and/or values for the personal standard values of a particular patient in the judging section on the other hand and the detected data, if judged to be abnormal, are sent out through the control section to the input/output interface and transmitted to the data processing facility of a medical organization by way of the telephone line.

The clinic or hospital (hereinafter sometime referred to collectively as a medical center) can properly recognize the daily state of a patient by the transmission of ordinary personal data stored continuously and also can rapidly cope with the patient's abnormal state by the abnormal data occassionally sent to the medical center. In the case of the abnormality information, since only those abnormality data requiring urgent treatment are selectively sent out by the comparison with standard values previously stored, frequent and wasteful operation of the system can be avoided, which would otherwise be caused, e.g., by trivial slight abnormalities, failure of sensors, etc. and would increase the burden on the side of the data processing facility.

In an embodiment where the wireless transmission system is employed between the transmission section and the receiving section, since only the transmission section is attached to the body of a patient, and the patient is physically isolated from the telephone set, his movement is set free from the connection with the telephone set, as well as there is less worry for the detachment or disconnection failure for connection cables, etc.

BRIEF DESCRIPTION OF THE ACCOMPANYING DRAWINGS

These and other objects, as well as the features of the present invention will become apparent by the detailed descriptions of the present invention by way of its preferred embodiments while referring to the accompanying drawings, wherein FIG. 1 is an explanatory view illustrating the conceptional appearance of one embodiment of the system for the centralized management of medical data according to the present invention;

DETAILED DESCRIPTION OF PREFERRED EMBODIMENT

The present invention will be explained referring to a preferred embodiment thereof shown in FIG. 1 through FIG. 4.

Figure 1:
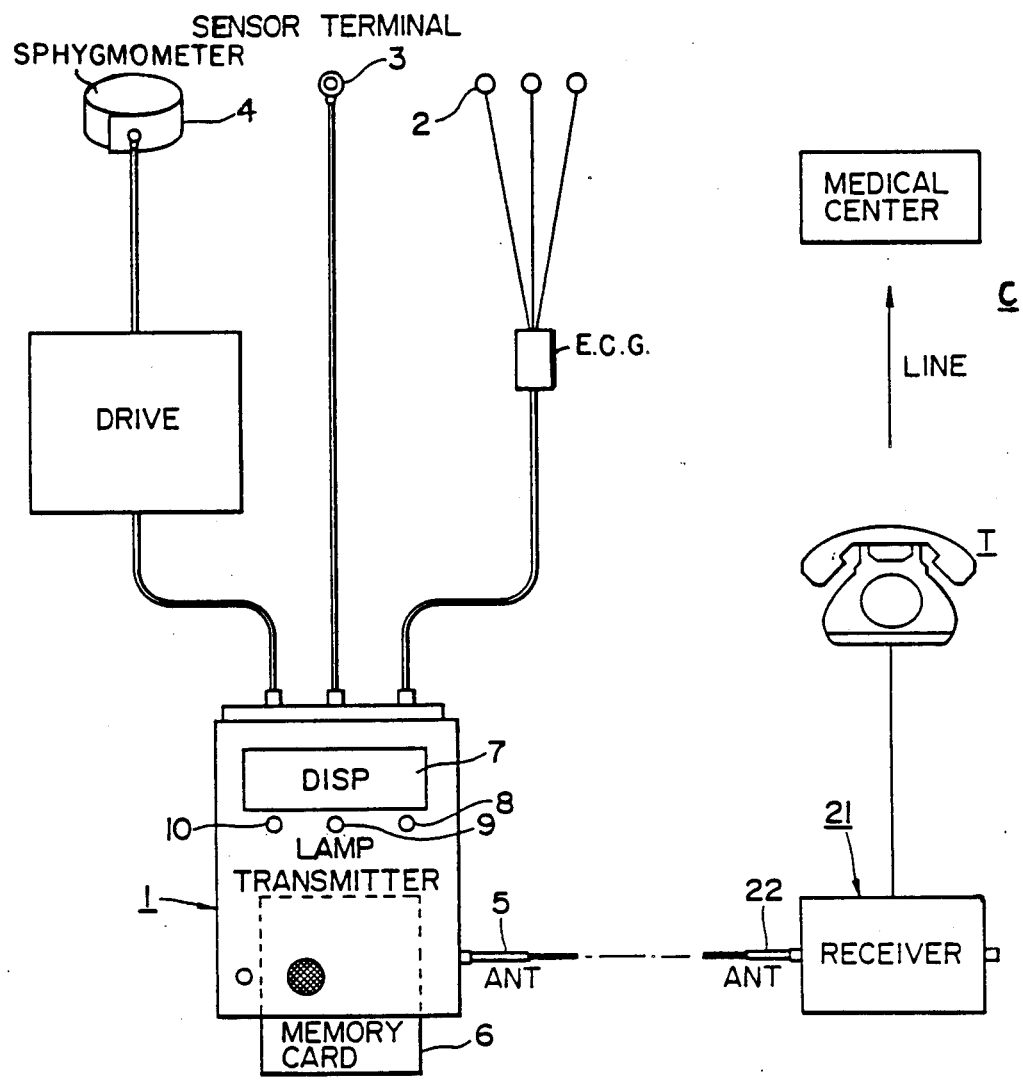
Figure 2:
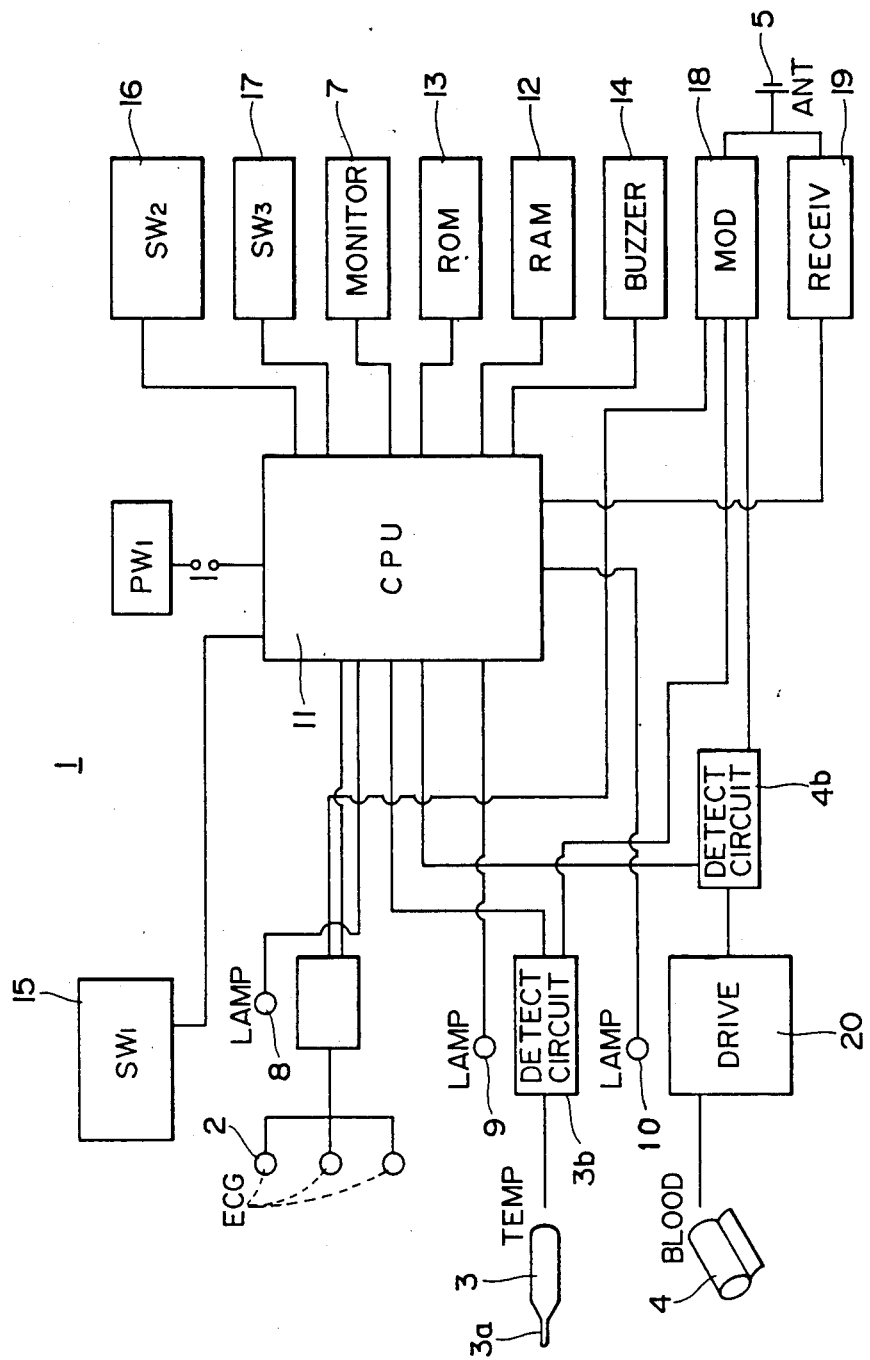
FIG. 2 is an outlined block diagram illustrating the constitution of the transmitting section in one embodiment of the system according to the present invention.
Figure 3:
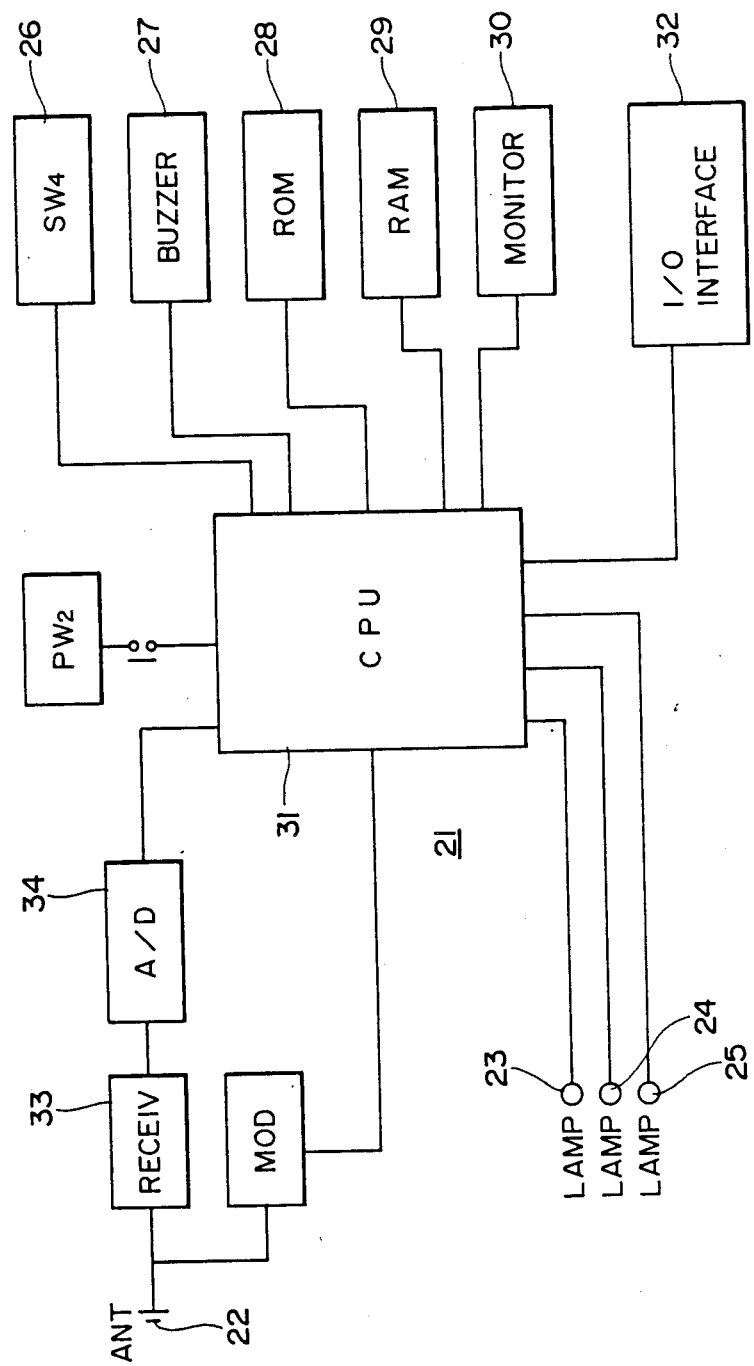
FIG. 3 is an outlined block diagram illustrating the constitution of the receiving section in one embodiment of the system according to the present invention.

In FIGS. 1–3 showing the fundamental concept of the system according to the present invention, there are shown a transmitter 1 as a transmission section and a receiver 21 as a receiving section. As shown in FIG. 1, an electrocardiograph 2, a thermometer 3 and sphygmomanometer 4 are connected as sensors for detecting bio-body data and connected to the transmitter 1.

A 3-electrode system is shown for the electrocardiograph 2 for simplifying the constitution, an electronic digital thermometer is used as the thermometer 3 and a $CO_2$ driven system is employed for the sphygmomanometer 4 for preventing noise in this embodiment. However the system is not always restricted to such types. In addition, sensors for detecting those bio-body informations other than the above, for example, a pulse meter, etc, may also be used depending on the purpose.

An antenna 5 is connected to the output of the transmitter 1 FM modulator 18 (FIG. 2) is used with the antenna 5 for transmitting the data indicative of bio-body information detected by respective sensors to the receiver 21 over a wireless channel. A magnetic IC memory card 6 is attached detachably to the system as a memory device (RAM 12) as described later. A monitor using liquid crystal display, etc. displays data and elements 8, 9 and 10 represent confirmation lamps for the operation of the respective sensors.

Antenna 22 is disposed on the input of the receiver 21 for receiving the data of the bio-body information from the antenna 5 of the transmitter 1 in the form of electromagnetic waves. An input/output interface 32 is disposed (FIG. 3) on the side of the output for automatically driving the telephone set T disposed at the home of a patient, to connect to the telephone set of a medical center C by way of a telephone line LINE. The receiver 1 and the transmitter 21 may also be coupled, for example, by an optical fiber cable. The data from each of the sensors attached to the patient, for example, data of the blood pressure from the sphygmomanometer 4 are sent by way of the logic sections in the transmitter 1 and/or the receiver 21 and the control section to the data processing facility of the medical center C by way of the telephone line LINE.

FIG. 2 is a block diagram showing one embodiment for the constitution of the transmitter 1. In the transmitter 1, a CPU (central processing unit) 11 has, connected thereto, terminals of the respective sensors described above, i.e., the electrocardiograph 2, the electronic thermometer 3 and the sphygmomanometer 4; the antenna 5 for the transmission; the monitor 7; lamps 8, 9, 10 showing the output from the respective sensors; RAM (random access memory) 12, ROM (read only memory) 13, warning buzzer 14, emergency transmission ($SW_1$) switch 15, ordinary transmission switch ($SW_2$) 16, confirmation switch ($SW_3$) 17, modulation circuit 18, receiving circuit 19, driving device 20 for the sphygmomanometer, power source $PW_1$, etc.

ROM 13 contains stored therein control programs for the various system operations conducted by the CPU 11. RAM 12 contains stored therein respective reference values for the medical data of bio-body information such as electrocardiogram, body temperature, blood pressure, etc. It also stores therein the data currently detected from a patient by the electrocardiograph 2, the electronic thermometer 3 and the sphygmomanometer 4 continuously for a predetermined period of time, for example, from 6 to 24 hours.

The temperature-sensing portion 3a of the electronic thermometer 3 is connected to a temperature detection circuit 3b for amplifying temperature signals, while the sphygmomanometer 4 is connected with a driving portion 20 consisting of a motor, a pump, etc. for supplying pressurized air to the cuff of the sphygmomanometer. A pressure detection circuit 4b is disposed for detecting whether the pressure of air sent from the driving section to the cuff is appropriate or not.

FIG. 3 is a block diagram illustrating one embodiment for the constitution of the receiver 21 in the system according to the present invention. In the receiver 21, a CPU 31 for controlling the operation of each of the sections has, connected thereto, lamps 23, 24 and 25 for respective sensors such as the electrocardiograph, thermometer and sphygmomanometer like those in the transmitter, a confirmation switch ($SW_4$) 26, warning buzzer 27, ROM 28, RAM 29, monitor 30, input/output interface 32, receiving circuit 33, A/D conversion circuit 34 power source $PW_2$, etc.

The ROM 28 contains stored therein programs for controlling various system operations of the CPU 31.

The RAM 29 contains, stored therein, like that the RAM 12 of the transmitter 1, various reference values for respective medical data. The RAM 29 also contains, stored therein, those medical data detected from the patient by the electrocardiograph 2, electronic temperature 3 and sphygmomanometer 4 and transmitted directly not passing through the CPU 11. Among the medical data passed through the CPU 11 on the side of the transmitter 1, the normal data are not transmitted to the receiver 21 because they are stored in RAM 29 and are excluded upon an abnormality check conducted by the CPU 11 in its function as the logic section. Accordingly, among the entire data, i.e., those including the normal data as well as abnormal data are retained are transmitted from the modulation circuit 18 of the transmitter 1 to the receiver 21 and the normal data are also stored in the RAM 29. This enables continuous storing of all the medical data including store the ordinary medical data of the particular patient in the RAM 29 and utilization, when necessary, by the medical center.

For the respective bio-body information detected by the respective sensors, for example, blood pressure, there are previously stored values for the general reference (normal) value and ranges (for example, 150 (max)/90 (min) for the sphygmomanometer 4), values for the personal ranges inherent to a particular patient, i.e., a personal permissible range (150 (max)/90 (min) - 190(max)/ 120(min)).

In addition, the respective bio-body information detected continuously for a predetermined period of time are stored as the personal standard values for the bio-body information to the inside of the RAMs 12, 29 of the transmitter 1 and the receiver 21.

These standard general and personal values and ranges may be stored in both the RAMs 12 and 29, in any desired combination while taking the hardware constitution or the like into consideration. Furthermore, it is possible to dispose the RAM side only to one side of the transmitter 1 and the receiver 21. Furthermore, the RAM may be in the form of a magnetic memory IC card detachable to the system as shown by the card 6 in FIG. 1. In this case, the memory card 6 written with the medical data may be detached from the transmitter 1 and sent to a card reader (not illustrated) for sending the data to the medical center. Alternatively the card can be carried about, for example, by a patient when he calls on the medical center.

In the system according to the present invention having the foregoing constitution, when the power sources $PW_1$ and $PW_2$ are turned ON, bio-body information such as electrocardiogram, body temperature, blood pressure, etc. are continuously detected from the respective sensors 2, 3 and 4 attached to the patient.

For instance, the value for the blood pressure detected by the sphygmomanometer 4 is detected and amplified by the pressure detection circuit 4b, directly transmitted from the modulation circuit 18 and the antenna 5 to the antenna 22 of the receiver 21 by wireless system and then stored by way of the CPU 31 to a predetermined memory region of RAM 29. When the data have been written to the RAM 29 to a predetermined memory capacity, or each time a predetermined of time is elapsed, the content is read out. For instance, if it is informed that the data have been accumulated for 24 hours, the signal indicating this is sent from the receiver 21 to the transmitter 1 and the transmitter 1 confirms it by the lamp display and also outputs an indication for reading the content of the RAM 29, by which the RAM 29 on the side of the receiver 21 is read out and the medical data stored in the RAM 29 is automatically sent out by way of the input/output interface 32 and through the telephone line L to the medical center C. The access for reading out the RAM 29 may alternatively be conducted from the outside (from the medical center).

Figure 4A:
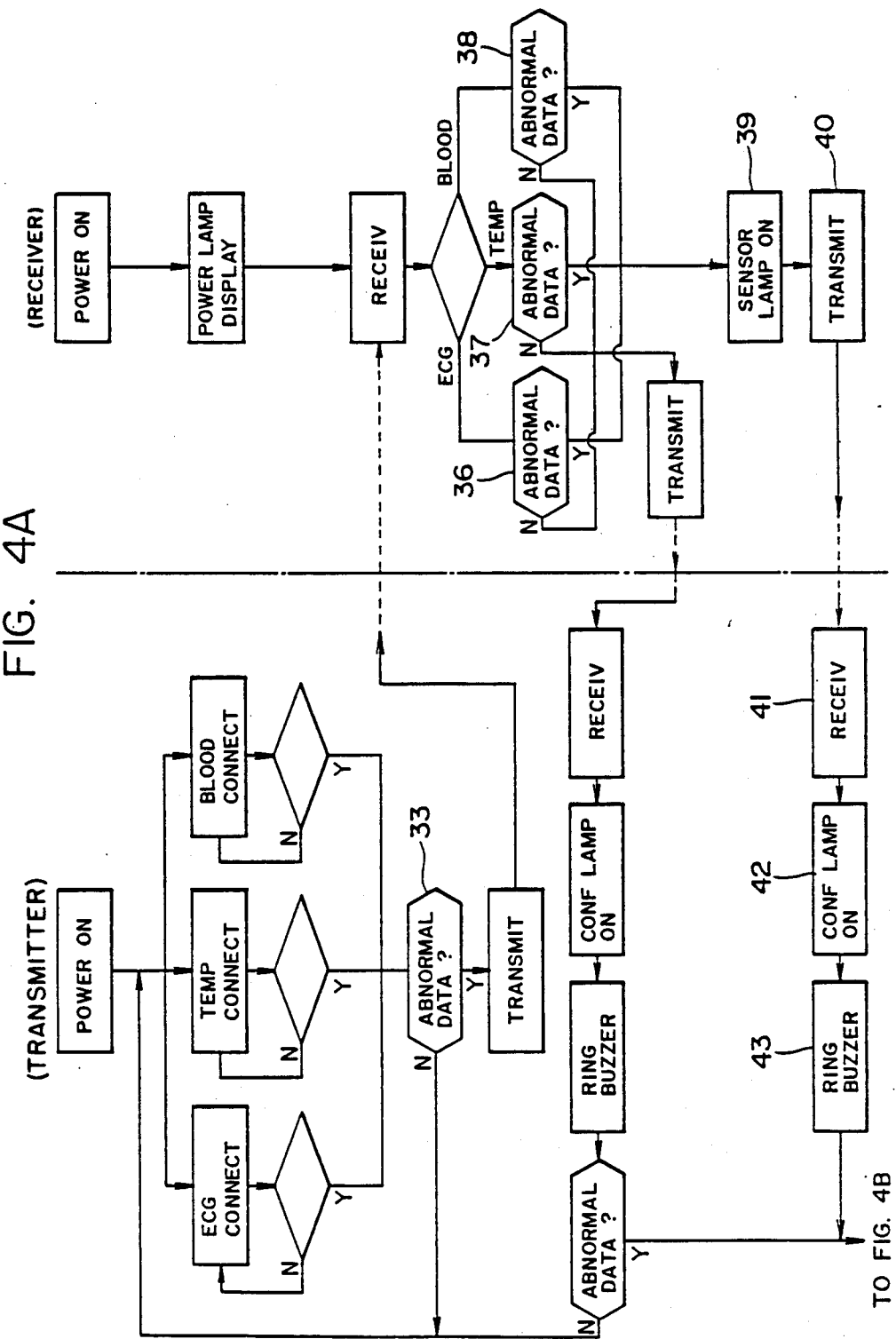
FIGS. 4A and 4B show a flow chart illustrating the outline for the abnormal detection operation of the system of one embodiment according to the present invention.
Figure 4B:
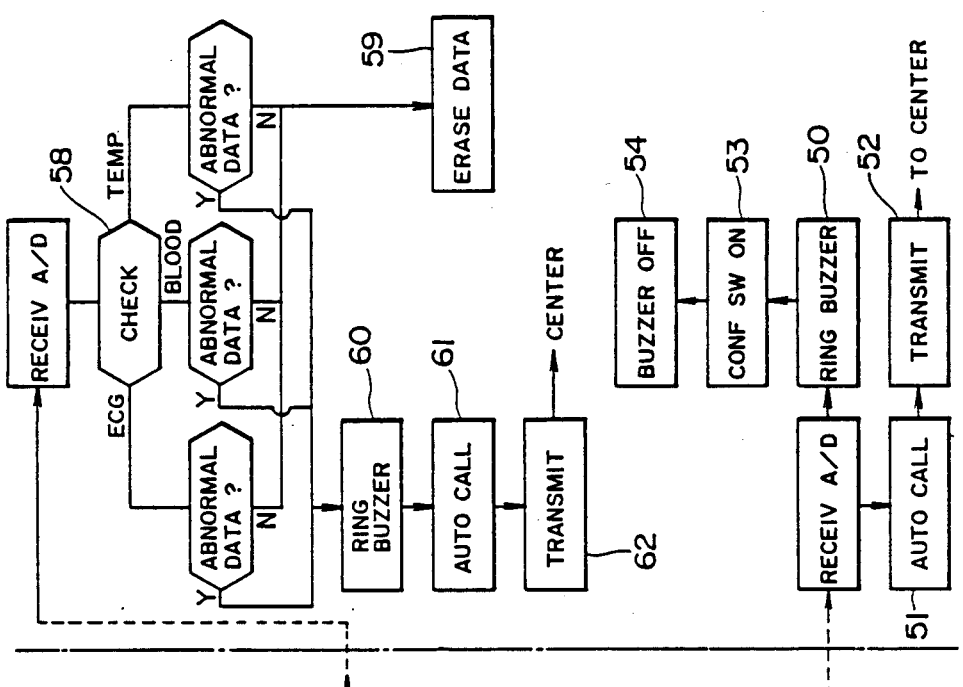
Figure 4B:
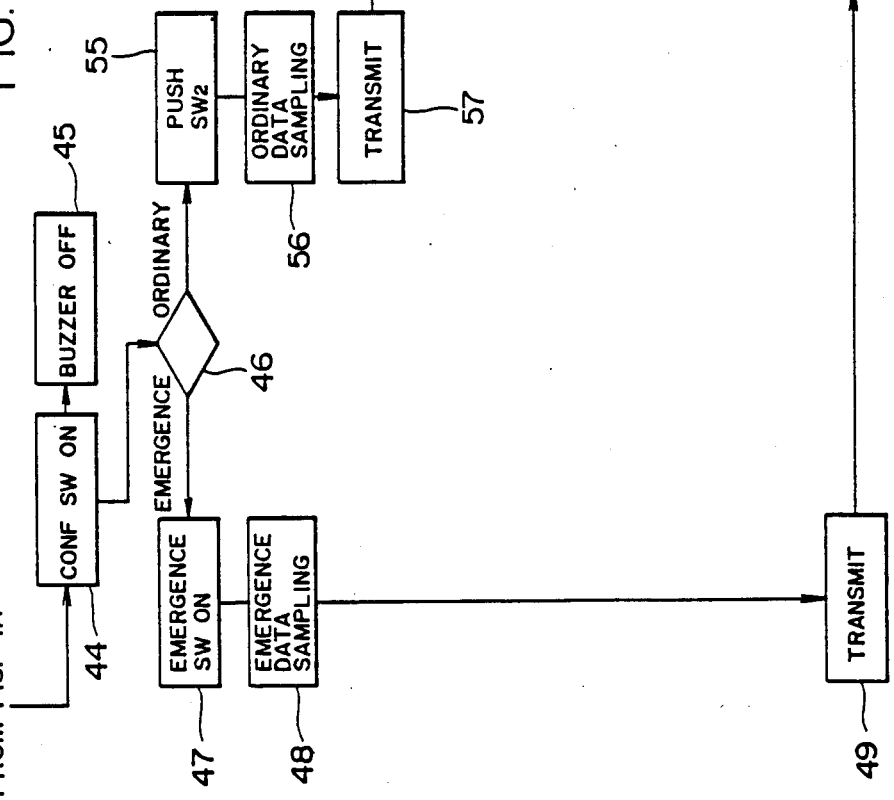

Explanation will now be made to the abnormal information operation of the system, for example, in a case where the value of the blood pressure detected from the sensor 4 of the transmitter 1 shows an abnormal state, while referring to the flow of FIG. 4A and 4B.

At first, the output detected from the sphygmomanometer 4 is compared with the value for the general standard range previously stored in the RAM 12 of the transmitter 1 by the CPU 11 that functions as a logic section (step 33). If step 33 judges abnormal data, that is the data is be out of the standard range at step 33, the data are sent from the transmitter 1 to the receiver 21.

The blood pressure data transmitted to the receiver 21 are sent by way of the receiving circuit 33 and A/D converter 34 to the CPU 31 that functions as the judging section. The CPU 31 compares the thus sent data with the values for the ordinary dangerous range previously stored in the RAM 29 for the blood pressure data (step 38) and, if it is judged to be in the dangerous range, the lamps 23, 24 and 25 are lighted up (step 39), and the signals are transmitted back to the transmitter step 40, and received by the transmitter at step 41. Then, the confirmation lamps 8, 9, 10 (in this case, lamp 10 for the sensor 4) is lighted up and the warning buzzer 14 is blown (steps 42 43). When the confirmation switch (SW₂) 16 is operated, blowing of the warning buzzer 14 is stopped (step 44, 45).

On the side of the receiver 1, the abnormal data are again examined by the comparison with the data for the personal permissible range of the blood pressure inherent to a patient stored in the RAM 12 (step 46). In a case where the data are judged to require emergency information to be sent to the Medical Center, the emergency data are accumulated on one hand in the RAM 12 (step 48), and also sent to the receiver (step 49) by the actuation of the emergency transmission switch (SW₁) 15.

The warning buzzer 27 is blown and subsequently extinguished (steps 50, 53, 54) on the side of the receiver 21. Simultaneously therewith, the emergency data are sent out by way of the I/O interface 32 and the telephone Line automatically to the medical center C (steps 51, 52).

If the abnormal data are judged to be at such an extent as requiring no emergency information although the data are not normal in the step 46, an ordinary transmission switch (SW₂) 16 is actuated (step 55) and the not-abnormal data are accumulated in RAM 12 (step 56).

The not-abnormal data are sent to the receiver 21 (step 57).

Then they are judged again on the side of the receiver 21 by comparison with the value for the personal permissible range inherent to the blood pressure value of a particular patient previously stored in the RAM 29 (step 58). If the amount of abnormality indicates a trivial amount of abnormality that is they are substantially equal to the normal value, the data are merely erased (step 59).

While on the other hand, if the not-abnormal data exceed the personal permissible range described above, the warning buzzer 27 on the side of the receiver 21 is blown (step 60) and, at the same time, the data are automatically informed by way of the telephone line Line to the medical center C (step 61, 62).

In the case where the data are judged not abnormal in the steps 36, 37, 38, the data are sent again to the transmitter 1 and the procedures of the flow are returned for checking as to if the terminal of the sensor, for example, the sphygmomanometer 4 is not detached or not.

In this way, when the abnormal data are informed, the medical center checks the abnormal data and, if they are of emergency, prepares the admission of the patient, or rapidly prepares an ambulance in a case where the patient's condition is serious.

In the system according to the present invention, since the accumulated medical data illustrating the daily store of an at-home patient, as well as abnormal medical data requiring urgent treatment are sent automatically by way of the telephone line to the medical facility, it is possible to always monitor the state of the at-home patient reliably and rapidly.

Furthermore, since the abnormal data for the respective sensors are compared with various kinds of standard ranges through several stages of judging steps and only the substantially abnormal data for a patient are immediately transmitted, the burden on the medical facility receiving such data can be moderated.

Furthermore, since the system is divided into a transmission section including sensors attached to a patient for detecting the bio-body information and a receiving section for processing the medical data and sending them with the telephone line, the patient's movement is relatively set free from the restriction to the system.

What is claimed is:

1. A system for centralized management of medical data regarding bio-body information detected from a patient by way of a telephone line to a data processing facility in a hospital, clinic or like other medical organization, said system comprising:
   a transmission section adapted to be attached to a patient and a receiving section situated remote from the patient, between which signals are sent;
   said transmission section including;
   at least one sensor adapted to be attached to a patient, for detecting bio-body information from said patient to produce a signal indicative thereof,
   at least one amplifier for amplifying said detected signal,
   an A/D converter for converting said amplified signal into digital bio-body data, and
   a transceiver for transmitting and receiving said bio-body data in a wireless mode relative to said receiving section,
   said receiving section having:
   a transceiver for transmitting and receiving said bio-body data in a wireless mode relative to said transmission section,
   a telephone set having an I/O interface connected to an external output of said receiving section:
   at least one of said transmission section and said receiving section, further including:
   a random access memory having a memory area means for storing predetermined reference values that define:
      (a) at least one kind of general standard ranges for bio-body information data which are determined each based on known average data taken from a certain group of healthy persons, and
      (b) at least one kind of permissible personal ranges for bio-body information data, of the same kind as said general standard range, and which are determined each depending on characteristics of a particular patient, and
   said random access memory also having another memory area means for continuously storing all of said bio-body information data detected by said at least one sensor within a predetermined period of time,
   a central processing unit having:
   means for receiving said bio-body information data,
   means for accessing said random access memory thereby fetching said reference values stored in said memory region selectively,
   means for comparing said bio-body information with said general standard ranges and then with said personal permissible range and with said corresponding reference values successively, and for determining whether said bio-body information require an emergency response, and means for outputting said bio-body information by way of said I/O interface of said receiving section, to said telephone line.

2. A system as defined in claim 1, wherein said reference values include values for systematic error ranges for checking physical failures of the system.

* * * * *